United States Patent [19]

Michael et al.

[11] 4,338,297

[45] Jul. 6, 1982

[54] POLYPEPTIDE ACTIVE POLLEN IMMUNOSUPPRESSANT FRACTION

[76] Inventors: Jacob G. Michael, 418 Chisholm Trail, Cincinnati, Ohio 45215; Amadeo J. Pesce, 5769 White Chapel Dr., Cincinnati, Ohio 45236

[21] Appl. No.: 139,881

[22] Filed: Apr. 14, 1980

[51] Int. Cl.³ .................... A61K 39/36; C07G 7/00
[52] U.S. Cl. ............................. 424/91; 260/112 R
[58] Field of Search ................ 424/91, 88, 177; 260/112 R, 112.5 R

[56] References Cited

PUBLICATIONS

Chemical Abstracts, vol. 81, p. 181, 1974, Abst. No. 2173e, "Chemical Modification of the Major Allergen of Ragweed Pollen, Antigen E".
Chemical Abstracts, vol. 82, p. 439, 1975, Abst. No. 55957r, "Immunogenic Properties of Modified Antigen E. II. Ability of Urea-Denatured Antigen and α-Polypeptide Chain".
Chemical Abstracts, vol. 83, p. 297, 1975, Abst. No. 191261g, "Immunogenic Properties of Modified Antigen E. III. Effect of Repeated Injections of Modified Antigen".
Takatsu, K., et al., J. Immunology, vol. 115, pp. 1469–1476, 1975.
King, T., et al., Immunochemistry, vol. 11, pp. 83–92, 1974.

*Primary Examiner*—Blondel Hazel

[57] ABSTRACT

Polypeptide active pollen immunosuppressant prepared by proteolytic enzyme digestion of pollen antigen and purified by reaction with antipollen antibody and therapeutic use thereof in desensitization.

1 Claim, No Drawings

POLYPEPTIDE ACTIVE POLLEN IMMUNOSUPPRESSANT FRACTION

BACKGROUND OF INVENTION

Hay fever, more particularly ragweed sensitivity, characterized classically by itching of the mucosa of the nose, mouth, pharynx and eyes, lacrimation, sneezing, watery nasal discharge, coughing and sometimes asthmatic wheezing, afflicts a considerable proportion of humans. Contact dermatitis may also be caused by ragweed pollen sensitivity manifested during the fall of the year. Untreated, the disturbance may disappear until the next season, but it may also become progressively worse, year by year and result in seriously discomforting asthma. Treatment initially entails trial of orally active antihistamines, sometimes in combination with sympathomimettes such as phenylpropanolamine or phenylephrine. The symtoms may thus be partially suppressed but the basic physiological difficulty, the histamine release by the antibody-antigen reaction, persists. For short periods of time, antiinflammatory corticoids may be administered. Commonly these treatments are inadequate or unsatisfactory and resort must be had to a more fundamental treatment, namely desensitization. Desensitization of human patients heretofore was accomplished by injections of extract of the offending pollen, in the case of ragweed sensitivity, extract of the pollen of ragweed (*Ambrosia artemisiae-folia*), to product in the patient an intercepting protective antibody. This deensitization is undertaken with extreme caution. Commencing with a very dilute preparation of ragweed allergen injected subcutaneously, if there is no local reaction within an hour of injection, the next dose is doubled and administered in 3 or 4 days. To be used in the event of an anaphylactic reaction, there must be available for emergency administration, adrenaline, antihistamines and intravenously administrable antiinflammatory corticosteroids during the testing and densitization procedures. Both the time and precautions accompanying the conventional ragweed densitization procedures are inconvenient.

This invention is concerned with the discovery, manufacture and use of a new and specific polypeptide active pollen immunosuppressant fraction, more particularly a ragweed segment that, upon administration to mammals including humans, effects protection against pollen or ragweed sensitivity without the accompanying and dangerous possibility of anaphylactic shock. Pollen allergen preparations of this invention are made from, illustratively, common ragweed, giant ragweed, rye (Groups I, II and III), June grass, orchard grass, sweet vernal grass, red top, timothy, yellow dock, wheat, corn, sagebrush, blue grass, California annual grass, pig weed, Bermuda grass, Russian thistle, mountain cedar, oak, box elder, sycamore, maple, elm, etc. Ragweed constitutes the most prevalent and noxious of these and is the primary example illustrated herein, the procedure being, of course, applicable to other pollen allergens in a like fashion. The instant new polypeptide active pollen immunosuppressant fractions, in contradistinction from prior art allergens, e.g. ragweed, can be administered in combination with adjuvants thus enhancing effectiveness of treatment without likelihood of anaphylaxis.

Unsuccessful previous attempts to achieve separation of protective and allergic inducing activities for the treatment of pollen sensitivities, particularly in ragweed-sensitive individuals have been reported. For example, Ishizaka, K., et al., J. Immunol. 113: 70–77, 1974 prepared four modifications of the active allergenic fraction of ragweed pollen extract, antigen E, obtained by ammonium sulfate gradient solubilization, namely urea denatured antigen E (UD), its alpha and beta polypeptide chains and a reduced carboxymethylated antigen E (RC). Both UD and RC lost antigenic determinants present in the unmodified antigen E and accordingly could not be used to achieve satisfactory antibody production against antigen E in humans. Each of the four preparations failed to combine with human gamma globulin, human Ig G, against the original native antigen, although they did not induce erythema wheal reactions in ragweed sensitive individuals. Since modified antigens do not induce allergenic reactions in the patients but are capable of stimulating T cells, carrier-specific helper cells, Ishizaka speculated that such modified antigens may change the T cell population without side effects. Subsequently, Ishizaka, et al., J. Immunol., 114: 110–115, 1975, reported that the urea-denatured antigen, UD, and the alpha-polypeptide chain isolated from the denatured antigen E importantly possess their own antigenic determinants different from and lacking in the major determinant of the undenatured molecule. While both native and Ishizaka modified antigens stimulated common T cells, mice immunized with the modified antigen formed a small amount of antibody against antigen E, thereby suggesting either contamination of the modified antigen with native protein or the presence of similar denatured protein in the test antigen E. In any event, Ishizaka states, the results collectively indicate that a major population of B cells stimulated by native antigen is different from the majority of B cells stimulated by the modified antigen. Further work on UD or alpha-polypeptide chain isolated from denatured molecules provided additional evidence that these materials undesirably prime T cells specific for native antigen E (Takatsu, et al., J. Immunol., 115: 1469–1476, 1975 and 116: 1257–1264, 1976). However, it must be recognized that the denatured protein and polypeptide chains obtained from the denatured protein themselves introduce foreign material which could aggravate allergic sensitivity by providing yet another foreign sensitizing material, over and above ragweed antigen, to which the body may react.

Investigation of the immunosuppressive properties of bovine serum albumin treated with pepsin to produce a peptic fragment resulted in a product which did not precipitate with antibody bovine serum albumin bud did inhibit the binding of specific antibody to labeled bovine serum albumin, thus indicating the presence of determinants found in the native antigen. This material could be used before immunization with bovine serum albumin in animals to cause significant suppression of allergic response with the suppression attributed to the presence of specific T suppressor cells in the body which are stimulated by the peptic fragment. By the present process of this invention, the original antigenic determinants are maintained as in the native molecule, Muckerheide A., Pesce, A. J., and Michael, J. G., J. Immunol., 119: 1340–1345, 1977. Further data support the concept that several types of determinants on complex protein antigens participate in the regulation of immune response and that separate determinants on the bovine serum albumin were responsible for immunogenic and suppressive properties of the antigen, Dosa, A., Pesce, A. J. Ford, O. J., Muckerheide, A., and Michael, J. G., Immunol., 38: 509-517, 1979. The art failed to show or suggest the preparation of a pollen desensitizing agent free of anaphylactic reactivity, such as could be used therapeutically.

FIELD OF THE INVENTION

We have now found that a safe and effective pollen desensitization material is preparable from pollen, illustratively ragweed pollen extract treated with proteolytic enzyme, inclusive of exopeptidases, e.g. carboxypeptidase A, and endopeptidases, e.g. trypsin, chymotrypsin, papain, particularly bacterial protease, nagarase, or pepsin, and then detoxified by affinity absorption to remove fractions exacerbating the allergy to be treated, to produce a product which possesses ability to suppress the immune response to antigen E, thereby avoiding anaphylactic dangers normally associated with attempted desensitization by use of antigen E, per se, ragweed pollen extract. The pollen allergen desensitizing product is obtained by proteolytic digestion of a primary pollen allergen to produce a pollen specific polypeptide fraction having a molecular weight of about 10,000, being free of disulfide bonds, rich in tyrosine, and removed therefrom are peptides reactive with antibody to the aforesaid pollen by affinity absorption with antibody to the aforesaid pollen. The instant immunosuppressive factor is not an antigen but may be used by itself or administered along with adjuvants to achieve greater efficacy in desensitization by blocking the immune response.

The product of this invention does not give a positive wheal and flare reaction in sensitive individuals, e.g. ragweed sensitive individuals, nor will it react in the passive cutaneous anaphylaxis reaction (PCA) in rats sensitized, e.g. by specific illustration, with ragweed antigen or antibody. While the instant, ragweed, pollen polypeptide is not an antigen, nevertheless it has been found that the efficacy of this polypeptide is suppressing immune response, in activating T cell suppression, and in blocking or inactivating B cells, is promoted by the conjoint or coadministration of the polypeptide with adjuvants known for use in conjunction with active allergens. Examples of adjuvants contemplated for this purpose are in Chedid, U.S. Pat. No. 4,094,971, acylated peptidoglycane saccharides; Jones, et al., U.S. Pat. Nos. 4,082,735 and 4,082,736. Whereas the adjuvants of Chedid, Jones, and others in the art are described as useful in conjunction with allergens, we have found an unexpected and important new use for allergen adjuvants, namely in conjunction with immunosuppressive agents rather than allergens, particularly in conjunction with the instant immunosuppressant, the polypeptide active pollen immunizing fraction.

DESCRIPTION OF PREFERRED EMBODIMENTS

PREPARATION 1

Short Rag Weed Extract and Fraction A

Defatted short ragweed pollen, 10 g, is added to distilled water, 50 ml, and stirred for 48 hours at 4° C., or optionally as little as 2 hours at 25° C. The slurry is filtered through paper on a Buchner funnel, the filtrate being whole ragweed pollen aqueous extract. To this extract, solid ammonium sulfate is added to 90% saturation and the mixture is maintained for 2 to 3 hours at 4° C. and centrifuged. The precipitate is separated and dissolved in 3.5 ml of 0.1 M TRIS buffer and 0.06 M HCl (pH 7.9). This buffered solution is run through a Sephadex G-25 polydextran molecular sieve column 95 cm high and 4 cm in diameter which has been equilibrated with 0.025 M TRIS and 0.015 M HCl (pH 7.9). The first peak raffinate from the column is Fraction A. To assure purification, Fraction A is optionally again passed through the column. The raffinate is centrifuged and the supernatant portion is lyophylized.

EXAMPLE 1

Lyophylized Fraction A from Preparation 1 is dissolved in a buffered aqueous solution of nagarase proteolytic enzyme from B. subtilis, 20 mg of nagarase per ml of 0.1 M sodium bicarbonate (pH 8.0) in a preparation of Fraction A 100 parts to nagarase 1 part. After incubation for 24 hours at room temperature the enzyme digestion is stopped by the addition of PMSF stock solution, 190 mg per ml of 0.1 M sodium bicarbonate (pH 8.0), added to the enzyme digest to produce a molarity ration of PMSF to nagarase of 1.5:1. This is the crude polypeptide active ragweed pollen immunizing fraction.

EXAMPLE 2

Lyophilized Fraction A from Preparation 1 is dissolved in 0.1 M sodium bicarbonate at a concentration of 200 mg of Fraction A per 10 ml of buffer solution and repeatedly slowly passed through a column of immobilized pepsin enzyme on glass beads. After 20 passages at room temperature the digest is removed from the column and lyophilized.

EXAMPLE 3

A citrate-phosphate buffer (pH 3.0) is prepared from 39.8 ml of 0.1 M citric acid and 10.2 ml of 0.2 M dibasic sodium phosphate diluted to 100 ml with distilled water. The lyophilized Fraction A from Preparation 1 is dissolved in this buffer solution in a proportion of 20 mg of Fraction A per ml of buffer. To this is added an aliquot of 5 mg of pepsin in 1 ml of distilled water to give a ration of Fraction A to pepsin of 100 to 1. The solution is maintained for 24 hours at room temperature and then brought to pH 7.4 by the addition of 0.1 M sodium hydroxide. The resulting ragweed pollen specific immunosuppressant has the ability to block immune response to antigen E but is in itself somewhat immunogenic.

EXAMPLE 4

The products of Examples 1, 2 and 3 are further purified by passing each of them through an affinity absorption column prepared as follows: Sepharose 2B polydextran molecular sieve coupling capability with proteins, is washed with distilled water. Sepharose, washed, 0.5 volume and distilled water 0.5 volume are added to 1 volume of 2 M sodium carbonate and stirred slowly. To this slurry, 0.5 volume of 2 g per ml of cyanogen bromide in acetonitrile is added all at once. The slurry is stirred vigorously for 2 minutes. The Sepharose is then washed with 10 volumes of 0.1 M sodium bicarbonate, pH 9.5. The slurry is filtered under vacuum and the filter cake is transferred to a flask containing 100 ml of 1 percent human ragweed gamma globulin in 2 M sodium bicarbonate. Coupling of the Sepharose and human ragweed gamma globulin is effected by maintaining the preparation at 4° C. for 20 hours. After coupling, the Sepharose beads are washed successively with 20 volumes each of 0.1 M sodium acetate, pH 4.0, 0.1 M sodium bicarbonate, and physiological saline.

Lowry determinations done before and after coupling demonstrate 86.3% efficiency of coupling of human gamma globulin to Sepharose beads.

The purified products of each of Examples 1, 2 and 3 obtained in this Example are substantially identical and free of peptides reactive with anti-ragweed antibody. The resulting unabsorbed allergen digest, the polypeptide active pollen immunosuppressive fraction (PAPIF) is used for the treatment of allergy. If desired, the raffinate may be lyophilized to produce a dry solid product which keeps well and may be resuspended in saline for therapeutic use.

This material prepared from ragweed pollen has a molecular weight of about 10,000. It is rich in tyrosine and contains no detectable disulfide bonds. Immunologically the substance does not inhibit the reaction between Fraction A and Fraction A antiserum.

EXAMPLE 5

To demonstrate the in vivo efficacy of PAPIF in mice, and its effect on Ig E antibody formation against ragweed, corresponding to sensitization, type $BDF_1$ mice were injected intraperitoneally with ragweed extract and alum as an adjuvant, test challenge material was then injected percutaneously with results as given in Table 1. Immune response was measured by passive cutaneous anaphylaxis (PCA) reaction in rat skin. Positive skin reaction indicates presence of Ig E sensitive antibodies. The cutaneous (PCA) challenge consisted of 1 mg ragweed extract dissolved in 1 ml of 1% Evans blue.

TABLE 1

| Preparation | 10 days | 40 days* |
|---|---|---|
| Ragweed Ext. 10 μg | 1:320 dilution | 1:1620 dilution |
| Ragweed Ext. 100 μg | 1:160 dilution | 1:1620 dilution |
| PAPIF 10 μg | 0 | 0 |
| PAPIF 100 μg | 0 | 0 |

*second injection was given at 30 days

The above data show complete lack of immunogenicity of PAPIF in both primary and secondary immune responses as compared with ragweed extract which effected responses at dilutions of 1:160 and 1:1620.

EXAMPLE 6

To test the effect of ragweed PAPIF as an immunosuppressant, mice were injected I.V. with PAPIF prior to immunization with ragweed extract in accordance with Table 2.

TABLE 2

| PAPIF | RAGWEED EXT. | PCA titer day 10 |
|---|---|---|
| 100 μg day 0 | 100 μg day 1 | 0 |
| 10 μg day 0 | " | 0 |
| 1 μg day 0 | " | 1:10 |
| 100 μg day 1 | " | 1:10 |
| 10 μg day 1 | " | 1:20 |
| 1 μg day 1 | " | 1:40 |
| 0 | " | 1:160 |

The data of Table 2 clearly show the immunosuppressive effect of PAPIF on the immune response to ragweed antigen in the primary immune response.

A similar degree of suppression by I.V. injection was observed during the secondary immune response to ragweed antigen in accordance with Table 3.

TABLE 3

| PAPIF | RAGWEED EXT. | PCA day 40 |
|---|---|---|
| 100 μg day 0, day 29 | 100 μg day 1, day 30 | 1:10 |
| 10 μg day 0, day 29 | " | 1:40 |
| 1 μg day 0, day 29 | " | 1:80 |
| 0 | " | 1:3200 |

The effects of PAPIF in the inhibition of ongoing immune response to ragweed antigen was also demonstrated. After Ig E response became evident the animals were injected I.V. with PAPIF in accordance with Table 4.

TABLE 4

| PAPIF | RAGWEED EXT. | PCA day 20 |
|---|---|---|
| Day 6,7,8 | Day 1 | |
| — | 100 μg | 1:160 |
| 100 μg | 100 μg | 1:10 |
| 100 μg | — | 0 |

Thus administration of PAPIF was suppressive even to ongoing Ig E response.

EXAMPLE 7

The PAPIF material of Example 4 was tested in humans either non-atopic or atopic specifically to ragweed antigen.

Fraction A and purified PAPIF were prepared at a concentration of 1 mg per ml in non-pyrogenic saline and filtered through a 0.25μ Millipore bacterial filter. The filtrate was further diluted with sterile isotonic saline to $10^{-3}$ to $10^{-6}$ dilutions and skin reactivity tested by intradermal injections of 0.02 ml per injection as follows:

In three non-atopic individuals, the $10^{-3}$ to $10^{-6}$ dilutions caused no skin reaction. This shows PAPIF at these concentrations to have no inherent reactivity in normal individuals.

In three atopic individuals, the following reactions were observed with the intensity of wheal graded from a maximum of plus four down to zero as reported in Table 5.

TABLE 5

| Dilution | Patient A | | Patient B | | Patient C | |
|---|---|---|---|---|---|---|
| | Fraction A | PAPIF | Fraction A | PAPIF | Fraction A | PAPIF |
| $10^{-3}$ | ++++ | +,0 | +++ | 0 | ++++ | +,0 |
| $10^{-4}$ | ++++ | 0 | ++ | 0 | ++++ | 0 |
| $10^{-5}$ | ++ | 0 | ++ | 0 | +++ | 0 |
| $10^{-6}$ | + | 0 | + | 0 | ++ | 0 |

In a typical case of pollen or ragweed allergy, desensitization is accomplished by treating the patient biweekly with PAPIF. Since PAPIF is relatively non-exacerbating, relatively large doses of it can be injected subcutaneously to achieve fast desensitization safely. For example, injection of 0.1 ml of $10^{-3}$ dilution of PAPIF (basic solution containing 1 mg of PAPIF per ml) is instituted biweekly for several weeks, desirably within three months prior to the beginning of the patient's ragweed sensitivity season. At the same time, the patient is tested by radioimmunoassay for concentration of specific antiragweed Ig E as well as for the skin reactivity to ragweed antigen. As a result of desensitization there is no increase in levels of antiragweed Ig E upon exposure of the individual to the ragweed. In addition, the reactivity of the desensitized individual to ragweed extract is significantly reduced.

We claim:

1. A safe and effective pollen desensitizing product from ragweed pollen produced by:
   (a) subjecting said ragweed pollen to controlled proteolytic enzymatic digestion using an enzyme selected from the group consisting essentially of nagarase, pepsin and immobilized pepsin to produce a specific degraded substance defined by a molecular weight of less than about 10,000, said substance being free of disulfide bonds and rich in tyrosine and possessing residuum active antigens, and
   (b) removing said residuum reactive antigens by reacting said degraded substance with a skin-sensitizing antipollen antibody to produce said pollen desensitizing product, which is non-reactive with said antipollen antibodies.

* * * * *